(12) United States Patent
Pearson, Jr. et al.

(10) Patent No.: US 8,737,705 B2
(45) Date of Patent: May 27, 2014

(54) METHOD AND APPARATUS FOR DETERMINING A SUBJECTS ORIENTATION

(75) Inventors: Phil E. Pearson, Jr., Hartland, WI (US); Scott Slavic, Sussex, WI (US); James Dodge, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 135 days.

(21) Appl. No.: 13/223,946

(22) Filed: Sep. 1, 2011

(65) Prior Publication Data

US 2013/0058545 A1    Mar. 7, 2013

(51) Int. Cl.
*G06K 9/00*    (2006.01)

(52) U.S. Cl.
USPC .......................................................... 382/128

(58) Field of Classification Search
None
See application file for complete search history.

(56) References Cited

U.S. PATENT DOCUMENTS

| | | | |
|---|---|---|---|
| 4,262,306 A | 4/1981 | Renner | |
| 5,117,829 A | 6/1992 | Miller et al. | |
| 7,206,462 B1* | 4/2007 | Betke et al. | 382/280 |
| 7,535,231 B2* | 5/2009 | Dewdney et al. | 324/320 |
| 7,881,767 B2 | 2/2011 | Strommer et al. | |
| 8,002,465 B2 | 8/2011 | Ahn | |
| 2005/0033149 A1* | 2/2005 | Strommer et al. | 600/407 |
| 2008/0159611 A1* | 7/2008 | Tao et al. | 382/131 |
| 2011/0228998 A1* | 9/2011 | Vaidya et al. | 382/131 |

* cited by examiner

*Primary Examiner* — Barry Drennan
*Assistant Examiner* — Siamak Harandi
(74) *Attorney, Agent, or Firm* — The Small Patent Law Group; Dean D. Small

(57) ABSTRACT

A method for determining a subject's orientation includes receiving, at an imaging system, an input that indicates an orientation of a subject being imaged, automatically determining the orientation of the subject using a feature recognition system, comparing the received input to the automatically determined orientation, and generating an image, the image including orientation indicia based on the comparison. An object orientation recognition system and an imaging system are also described herein.

20 Claims, 5 Drawing Sheets

METHOD AND APPARATUS FOR DETERMINING A SUBJECTS ORIENTATION

BACKGROUND OF THE INVENTION

This subject matter disclosed herein relates generally to imaging systems, and more particularly, to a method and apparatus for determining an orientation of a subject using an imaging system.

Medical imaging systems are used in different applications to image different regions or areas (e.g., different organs) of a patient. For example, a computed tomography (CT) imaging system may be utilized to generate images of a patient's bones or organs. In operation, an operator manually enters information that is utilized to perform a scan of the patient. Such information may include, for example, the patient's name, the patient's sex, and various scan protocols that define the radiation dosage to be delivered to the patient during the scan.

Additionally, the operator manually enters the patient's orientation. The patient's orientation indicates the position of the patient on the imaging table, for example, whether the patient is being positioned face up, face down, etc. during the imaging procedure. The patient's orientation, as entered by the operator, is then printed on at least one of the reconstructed images to enable a physician to perform a medical diagnosis. The orientation information printed on the image enables a physician to generally identify the locations of various organs and other items of interest such as, or example, a lesion. The orientation information may include a left indicator and a right indicator printed on the image. The left and right indicators generally refer to the left and right side of the images, respectively. Accordingly, when the patient is being imaged in the supine position, the left lung is expected to appear on the left side of the image and the right lung is expected to appear on the right side of the image.

However, the operator may inadvertently enter an incorrect patient orientation into the imaging system. For example, the operator may enter information that indicates that the patient is being imaged head first in the prone position when in fact the patient is in the supine position. In this case, the left lung would appear on the right side of the image and the right lung would appear on the left side of the image. While it should be appreciated that physicians have the medical skills to determine that the generated image reflects a different orientation than the orientation information printed on the image, the incorrect orientation information may still result in the physician spending additional time to perform the diagnosis. More specifically, the physician may have to first determine the correct orientation of the image and then perform the diagnosis. As a result, incorrect orientation information entered by the operator may result in an increased time to perform the diagnosis and in some cases may cause the physician to render an incorrect diagnosis.

BRIEF DESCRIPTION OF THE INVENTION

In one embodiment, a method for imaging a subject is provided. The method includes receiving, at an imaging system, an input that indicates an orientation of a subject being imaged, automatically determining the orientation of the subject using a feature recognition system, comparing the received input to the automatically determined orientation, and generating an image, the image including orientation indicia based on the comparison.

In another embodiment, an object orientation recognition system (OORS) is provided. The OORS includes at least one feature recognition device, and an object orientation recognition module (OORM) configured to receive a user input that indicates an orientation of a subject being imaged, receive an input from the feature recognition device that indicates the orientation of the subject, compare the user input to the input received from the feature recognition device, and generate an image, the image including orientation indicia based on the comparison.

In a further embodiment, an imaging system for generating an image of a subject is provided. The imaging system includes an object orientation recognition system (OORS). The OORS includes at least one feature recognition device, and an object orientation recognition module (OORM) configured to receive a user input that indicates an orientation of a subject being imaged, receive an input from the feature recognition device that indicates the orientation of the subject, compare the user input to the input received from the feature recognition device, and generate an image, the image including orientation indicia based on the comparison.

DETAILED DESCRIPTION OF THE INVENTION

Figure 1:
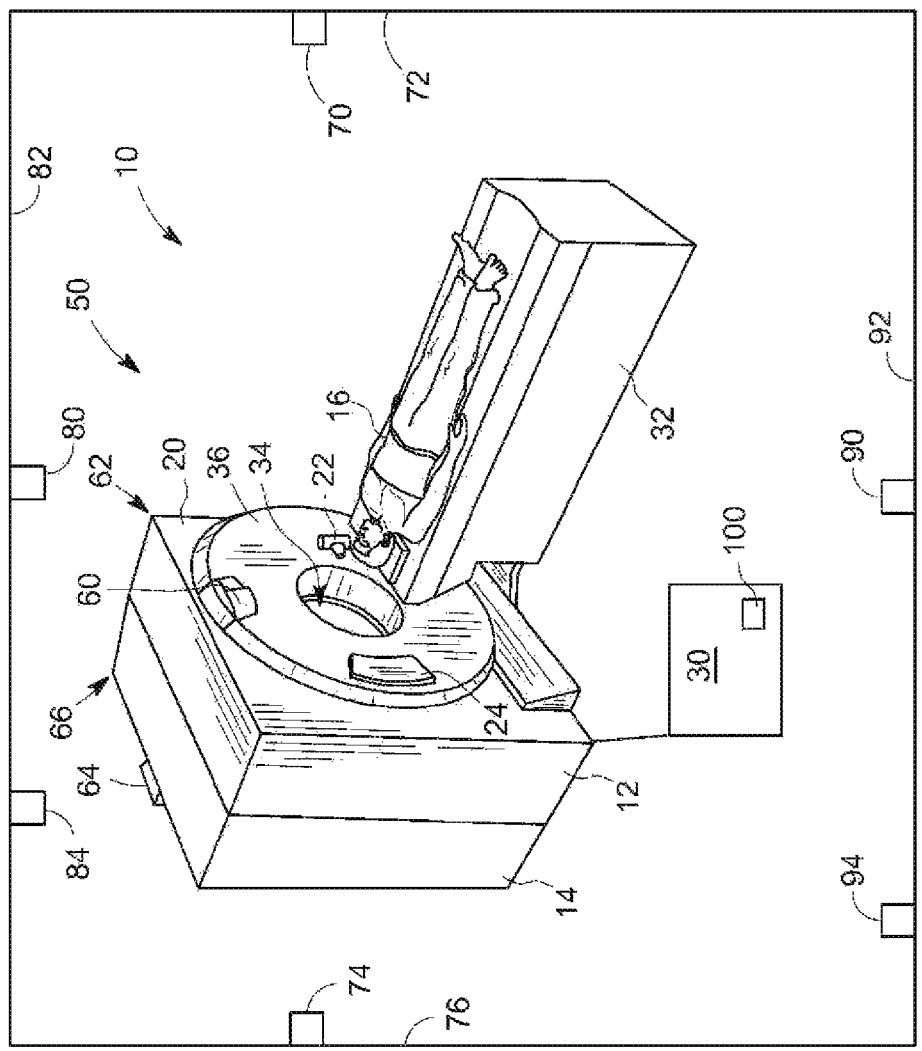
FIG. 1 is a pictorial view of an exemplary multi-modality imaging system formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 is a pictorial view of an exemplary imaging system 10 that is formed in accordance with various embodiments. Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used.

Referring to FIG. 1, the multi-modality imaging system 10 is illustrated, and includes a first modality unit 12 and a second modality unit 14. The two modality units, 12 and 14, enable the imaging system 10 to scan a subject 16 in a first modality using the first modality unit 12 and to scan the subject 16 in a second modality using the second modality unit 14. The imaging system 10 allows for multiple scans in different modalities to facilitate an increased diagnostic capability over single modality systems. In one embodiment, the multi-modality imaging system 10 is a CT/PET imaging system 10. Optionally, modalities other than CT and PET are employed with the imaging system 10. For example, the imaging system 10 may be a standalone CT imaging system, a standalone PET imaging system, a magnetic resonance imaging (MM) system, an ultrasound imaging system, an X-ray imaging system, and/or a single photon emission computed tomography (SPECT) imaging system, and combinations thereof, among others.

The first modality unit 12, e.g. the CT imaging system, includes a gantry 20 that has an x-ray source 22 that projects a beam of x-rays toward a detector array 24 on the opposite side of the gantry 20. The detector array 24 includes a plurality of detector elements (not shown), that are arranged in rows and channels that together sense the projected x-rays that pass through an object, such as the subject 16. The imaging system 10 also includes a computer 30 that receives the projection data from the detector array 24 and processes the projection data to reconstruct an image of the subject 16. In operation, operator supplied commands and parameters are used by the computer 30 to provide control signals and information to reposition a motorized table 32. More specifically, the motorized table 32 is utilized to move the subject into and out of the gantry 20. Particularly, the table 32 moves at least a portion of the subject 16 through a gantry opening 34 into a gantry bore 36.

The imaging system 10 also includes an object orientation recognition system (OORS) 50 that is configured to determine an orientation of an object, such as the subject 16, prior to and/or while the subject 16 is disposed within the imaging system 10. The OORS 50 includes at least one digital camera. In the exemplary embodiment, the OORS 50 includes a plurality of digital cameras. For example, the OORS 50 may include a first digital camera 60 that is coupled to a first side 62 of the gantry 20 and a second digital camera 64 that is coupled to an opposing second side 66 of the gantry 20. In the exemplary embodiment, the first side 62 represents an entry point for the subject 16 entering the bore 36 and the camera 60 is configured to acquire an image of the subject 16 prior to the subject 16 moving through the gantry opening 34 into the gantry bore 36. Moreover, the camera 64 is located on the second side 66 and may be configured to acquire an image of the subject 16 while the subject 16 is positioned within the gantry bore 36. Optionally, the second side 66 of the gantry 20 may represent an entry point for the subject 16 entering the bore 36 and the camera 64 is therefore configured to acquire an image of the subject 16 prior to the subject 16 moving through the gantry opening 34 into the gantry bore 36. Moreover, the camera 60 may be configured to acquire an image of the subject 16 while the subject 16 is positioned within the gantry bore 36.

Accordingly, and in the exemplary embodiment, the OORS 50 includes at least two cameras, one camera to image the subject 16 entering the bore 36 and a second camera to image the subject 16 while the subject 16 is positioned within the bore 36. The OORS 50 may also include a camera 70 that is mounted on a wall 72 and a camera 74 that is mounted on an opposing wall 74. In operation, the camera 70 may be configured to acquire an image of the subject 16 entering the bore 36 and the camera 74 may be configured to acquire an image of the subject 16 while the subject 16 is disposed within the bore 36. In a further embodiment, the OORS 50 may include a camera 80 that is mounted on a ceiling 82 and a camera 84 that is also mounted on the ceiling 82. In operation, the camera 80 may be configured to acquire an image of the subject 16 entering the bore 36 and the camera 84 may be configured to acquire an image of the subject 16 while the subject 16 is disposed within the bore 36. In still another embodiment, the OORS 50 may include a camera 90 that is mounted on a floor 92 and a camera 94 that is also mounted on the floor 92. In operation, the camera 90 may be configured to acquire an image of the subject 16 entering the bore 36 and the camera 94 may be configured to acquire an image of the subject 16 while the subject 16 is disposed within the bore 36. It should be realized that any combination and configuration of the cameras described herein may be utilized to acquire an image of the subject 16 either entering the bore 36 or while the subject 16 is positioned within the bore 36.

The cameras 70, 74, 80, 84, 90, and 94 may be embodied as either a camera that is configured to acquire a single digital image or a streaming video camera that is configured to acquire and store thousands of images of the subject 16. More specifically, the cameras described herein are configured to acquire and store an image of the subject 16. The stored image may then be transmitted and stored in a remote computer, such as for example, the computer 30. Thus, various embodiments provide at least one camera that is configured to acquire a still image or a moving image. For example, at least one of the cameras may be configured to acquire a plurality of two-dimensional (2D) images. The 2D images may then be combined to form a three-dimensional (3D) image of the subject 16. Moreover, at least one of the cameras may be configured to acquire a plurality of 2D images over a predetermined time period, e.g., a streaming video of the subject. In the exemplary embodiment, the images acquired by the cameras are utilized by the OORS 50 to perform in accordance with various embodiments described herein.

Moreover, it should be realized that the cameras described herein may also be utilized to perform a positive identification of a patient. For example, a picture of the patient may be acquired using any of the cameras described herein. The picture of the patient may then be placed in the patient's record for the examination.

Additionally, the cameras described herein may be embodied as infrared camera sensors, x-ray detection sensors or cameras, and the like. For example, assume that at least one of the cameras described herein is embodied as an x-ray detector. In operation, a scout scan of the patient may be performed before the axial/helical diagnosis scan. The information acquired from the x-ray detector may then be utilized to determine the patient's orientation. Thus, the information acquired from the x-ray detector may then be utilized to query the operator prior to the operator performing the diagnosis scan. It should be realized that conventional imaging systems may be modified to utilize the x-ray detector information to determine the patient's orientation.

The OORS 50 also includes an object orientation recognition module (OORM) 100. The OORM 100 is configured to automatically determine a position of the subject 16 while the subject 16 is positioned on the table 32. In the exemplary embodiment, the OORM 100 is configured to receive the images generated by the cameras 70, 74, 80, 84, 90, and 94 to automatically determine an orientation of the subject 16. The OORM 100 may be implemented as a piece of hardware that is installed in the computer 30. Optionally, the OORM 100 may be implemented as a set of instructions that are installed on the computer 30. The set of instructions may be stand alone programs, may be incorporated as subroutines in an operating system installed on the computer 30, may be functions in an installed software package on the computer 30, and the like. It should be understood that the various embodiments are not limited to the arrangements and instrumentality shown in the drawings.

Figure 2:
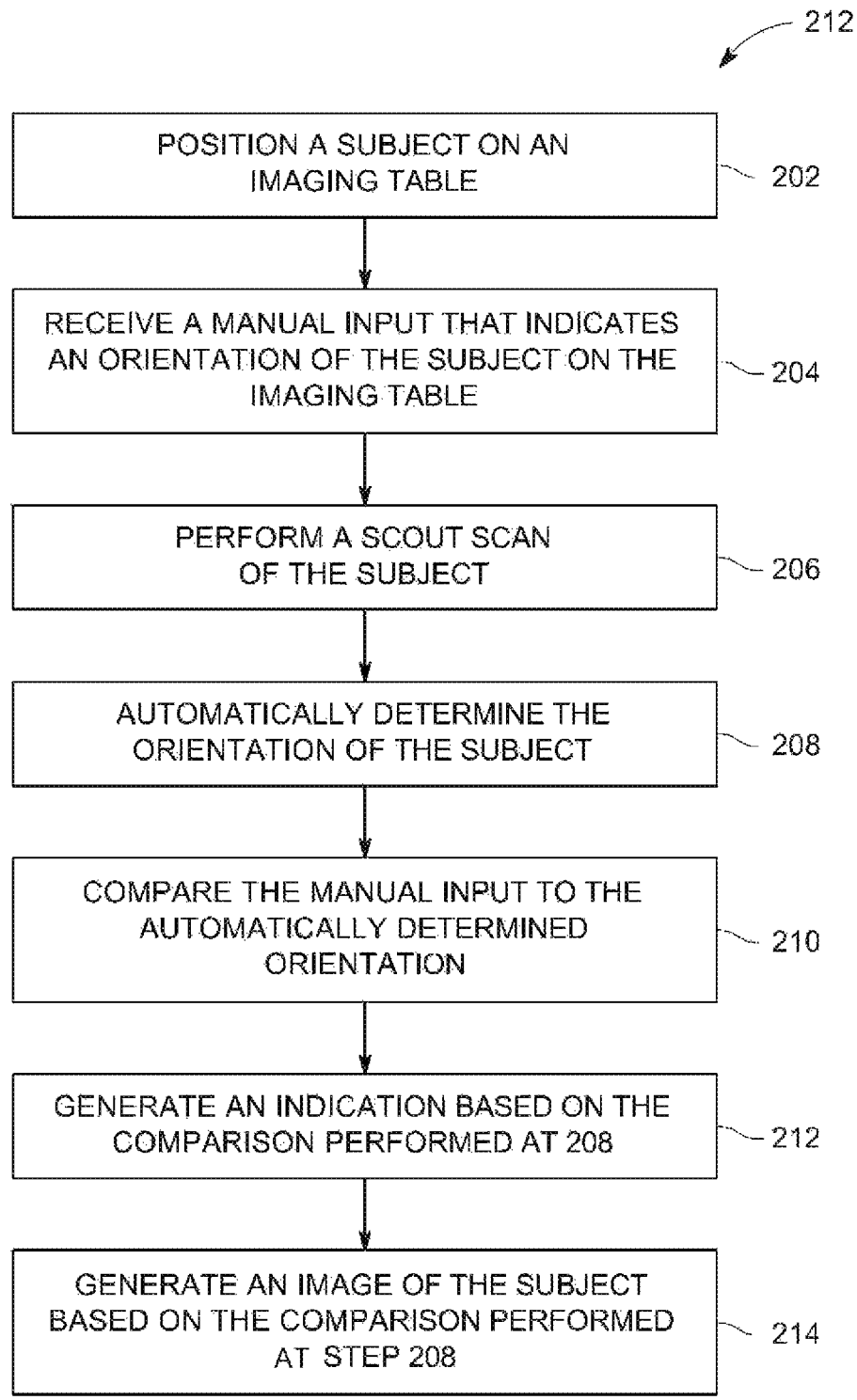
FIG. 2 is a flowchart illustrating an exemplary method for determining a subject's orientation in accordance with various embodiments.

FIG. 2 is a flowchart of an exemplary method 200 for determining a subject's orientation. The method 200 may be embodied as a set of instructions that are stored on the computer 30 and implemented using the OORM 100, for example. In various embodiments, the method 200 determines the orientation of the subject 16 and generates a visual indication when the subject 16 is not in the same orientation as the orientation manually entered by the operator.

At 202, a subject is positioned on an imaging table. For example, the subject 16 may be positioned on the imaging table 32 of the imaging system 10. The subject may be positioned in the supine position in which the subject is lying on his/her back. The subject 16 may be positioned in a prone position where the subject is laying on his/her stomach. The subject 16 may be positioned in a side position in which the subject is lying on one side or the other. The subject 16 may positioned in a head first position, also referred to as a superior position, wherein the subject's head is positioned to enter the bore 36 prior to the subject's feet. The subject 16 may also be positioned in an inferior position wherein the subject's feet are positioned to enter the bore 36 prior to the subject's head. It should be realized that the above positions are also referred to herein as subject orientations. As such, the orientation represents the physical position of the subject while disposed on the table 32 and the physical position of the subject with respect to the imaging system itself.

Figure 3:
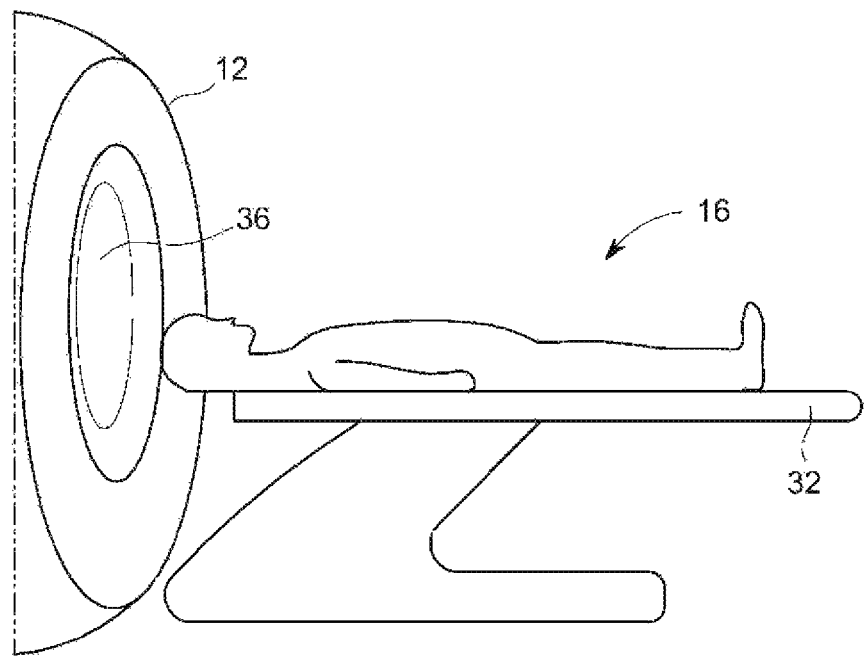
FIG. 3 is a side view of a subject positioned in an exemplary orientation in accordance with various embodiments.
Figure 4:
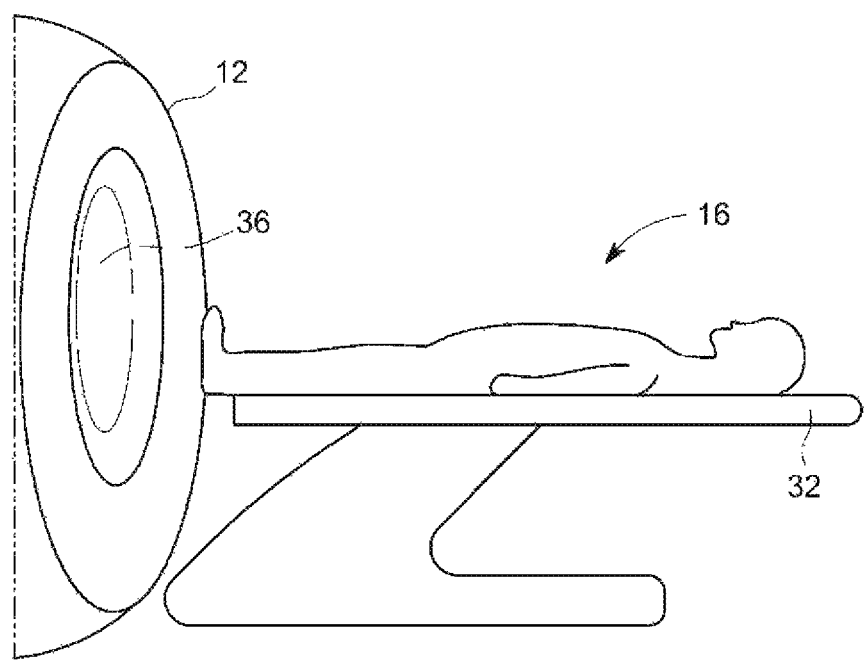
FIG. 4 is a side view of a subject positioned in another exemplary orientation in accordance with various embodiments.

It should also be realized that the above described subject orientations are exemplary and that the subject being imaged may be placed in other orientations that are not described herein. For example, the operator may request that the subject 16 lie in a supine/superior position on the imaging table 32, wherein the subject 16 is positioned face up with the head being positioned to enter the gantry prior to the feet as shown in FIG. 3. Optionally, the operator may request that the subject 16 lie in a supine/inferior position wherein the subject 16 is positioned face up with the feet being positioned to enter the gantry prior to the head as shown in FIG. 4. Optionally, the subject 16 may be placed in a prone/superior position, a prone/inferior position, or any other positions, for example, in other imaging systems, the subject 16 may be in a inclined, reclined or seated position.

Referring again to FIG. 2, at 204, an input is received that indicates an orientation of the subject 16 on the table 32. In the exemplary embodiment, the input is manually entered by the operator into the computer 30 and should represent the subject's orientation on the table 32. For example, the operator may manually enter orientation information that represents the orientation of the subject 16 as shown in FIG. 3 or may manually enter orientation information that represents the orientation of the subject 16 as shown in FIG. 4.

In another embodiment, the method 100 may be implemented without receiving the manual input for the operator. More specifically, the OORM 100 may be configured to automatically determine the orientation of the subject 16 using the feature recognition algorithm. The operator may then be prompted to confirm the results generated by the OORM 100. The results of the automatic determination may then be used to generate an image of the subject 16, the image including indicia indicating the orientation of the subject 16.

At 206, and in the exemplary embodiment, a scout scan of the subject 16 is performed. More specifically, the subject 16 is moved into the bore of the imaging system 10. A low dose scan of the subject 16 is then performed. More specifically, the scout scan, which may be either a lateral or anterior/posterior (A/P) scout scan, is performed to generate a scout image, which is generally a low resolution image of the subject 16. The scout scan image is then utilized to identify anatomical regions or landmarks within the subject to refine the locations to be imaged during the full imaging procedure. Optionally, the scout scan is not acquired at step 206. Rather, the method 200 proceeds from step 204 directly to step 208.

At 208, the orientation of the subject is automatically determined. In the exemplary embodiment, the orientation of the subject is automatically determined using the OORS 50. It should be realized that although the exemplary embodiment is described using the camera 60, any of the cameras described herein may be utilized to implement the method 200. In operation, the camera 60 acquires at least one image 102 of the subject 16 disposed on the table 32 as shown in FIG. 1. In the exemplary embodiment, the image 102 is acquired prior to the subject 16 being positioned within the bore 36 of the imaging system 10. Accordingly, the image 102 is preferably acquired while the subject 16 is located externally from the imaging system 10, e.g. outside the bore 36. Optionally, the camera 60 may acquire a plurality of images 102, e.g., a streaming video of the subject 16.

In operation, the OORM 100 operates as a feature recognition system that utilizes a feature recognition algorithm to automatically determine the orientation of the subject 16 using the image 102 received from, for example, the camera 60. Accordingly, in one embodiment, the image 102 is of the subject's face and the OORM 100 is configured to automatically perform a facial recognition analysis to determine whether the subject 16 is in a supine position or a prone position and whether the subject 16 is in a superior position or an inferior position. For example, the feature recognition algorithm may attempt to identify a nose, mouth, eyes, etc. of the subject 16. Optionally, the feature recognition algorithm may compare the features acquired in the digital image to a database of known features. Based on this comparison, the feature recognition algorithm may the output the results, or orientation of the subject, based on the comparison.

In another embodiment, the image 102 is of the subject's feet and the OORM 100 is configured to automatically perform a feet recognition analysis to determine whether the subject 16 is in a supine position or a prone position and whether the subject 16 is in a superior position or an inferior position. In other embodiments, images of other features of the subject 16 may be utilized to determine the orientation of the subject 16. For example, images of the subject's hands, etc. may be used to a data points for the feature recognition analysis. In the exemplary embodiment, the OORM 100 is embodied as a set of instructions that are installed on the computer 30. In operation, the image 102 acquired by the camera 60 is transmitted to the OORM 100 for analysis. Additionally, the input generated at step 202 is also input to the OORM 100 for analysis.

At step 210, the manual orientation information entered by the operator at step 202 is compared to the automatic feature recognition results generated at step 208. More specifically, the OORM 100 automatically analyzes the image 102 to determine the orientation of the subject 16. The OORM 100 then compares the automatically determined orientation to the orientation that was previously manually input by the operator at step 202.

Figure 5:
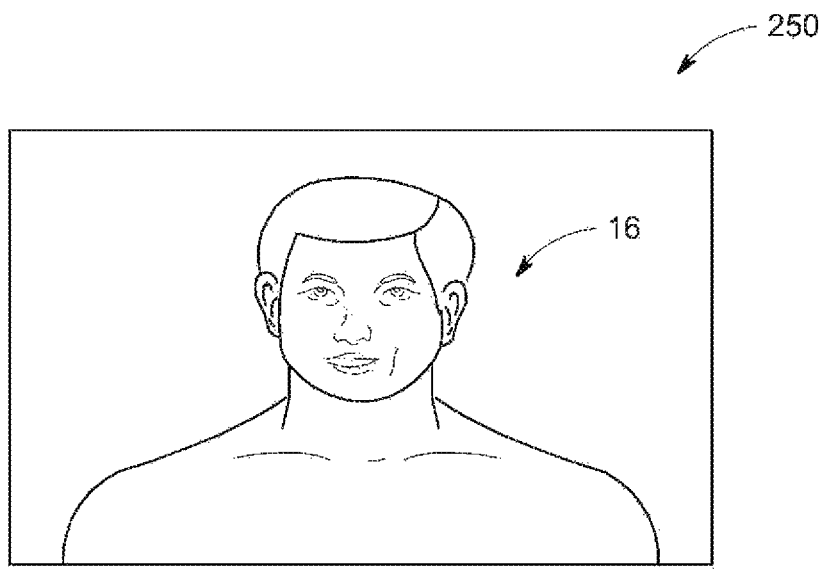
FIG. 5 is an exemplary image that may be generated in accordance with various embodiments.

For example, in one embodiment, assume that the subject 16 is positioned by the operator in a supine/superior position as shown in FIG. 3. Moreover, assume that the operator manual enters information into the imaging system 10 that indicates that the subject 16 is positioned in the supine/superior position. Further, assume that the picture 250 shown in FIG. 5 is received by the OORM 100 from the camera 60. Accordingly, when the feature recognition analysis is performed on the picture 250, the OORM 100 may automatically determine that the subject 16 is positioned in the supine/superior position based on the indication that the subject's eyes, ears, nose, and/or mouth are visible in the picture 250 and in the upright position. Thus, the subject's is being inserted head first into the bore 36. The results of the OORM 100, e.g. that the subject 16 is in the supine/superior orientation, are then compared to the manual orientation input received from the operator, e.g. that the subject 16 is in the supine/superior orientation. In this embodiment, because the results of the automatic feature analysis are the same as the manual input received from the operator, the method proceeds to step 212.

Figure 6:
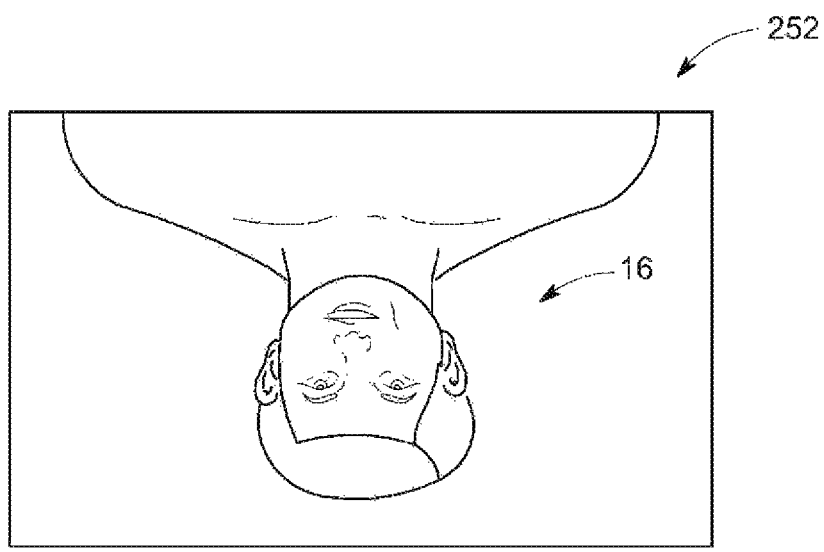
FIG. 6 is another exemplary image that may be generated in accordance with various embodiments.

As another example, assume that the subject 16 is positioned by the operator in a supine/superior position as shown in FIG. 3. Moreover, assume that the operator manual enters information into the imaging system 10 that indicates that the subject 16 is actually positioned in the supine/inferior position as shown in FIG. 4. Further assume that picture 252 shown in FIG. 6 received by the OORM 100 from the camera 60. Accordingly, when the feature recognition analysis is performed on the picture 252, the OORM 100 may automatically determine that the subject 16 is positioned in the supine/inferior orientation based on the indication that the subject's eyes, ears, nose, and/or mouth are visible in the picture 250 and in an upside down position. Thus, the subject's is being inserted feet first into the bore 36.

Figure 8:
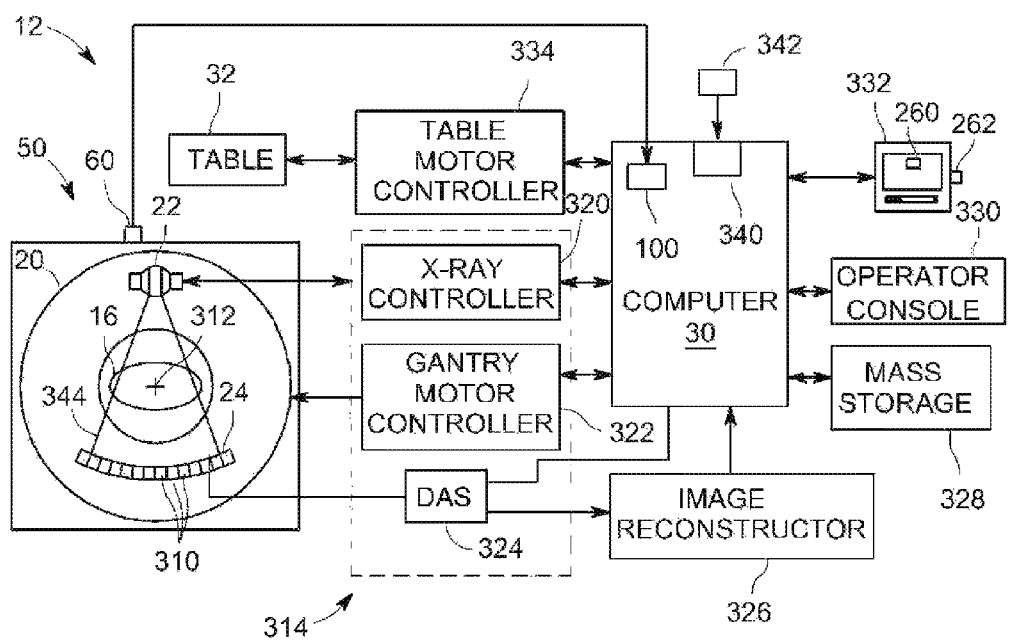
FIG. 8 is a block schematic diagram of one modality unit that forms part of the system illustrated in FIG. 1.

The results of the OORM 100, that the subject 16 is in the supine/inferior orientation, are then compared to the manual orientation input received from the operator, namely that the subject 16 is in the supine/superior orientation. In this embodiment, because the results of the automatic feature analysis are different than the manual input received from the operator, an indication is generated, at step 212, to inform the operator that the results of the automatically determined orientation generated at step 208 are different than the manual input received at step 202. In one embodiment, a visual indication 260, shown in FIG. 8, is generated. The visual indication 260 may be embodied as a light or as text on an imaging system display 332. Optionally, the indication may be an audio indication 262, also shown in FIG. 1, that is generated by the imaging system 10.

In one embodiment, the visual or audio indications, 260 or 262, are utilized to prompt the operator to input another orientation at step 202. The method then repeats steps 204-210 until the input at step 202 is the same as the output from step 208. In another embodiment, the OORM 100 is configured to automatically change the orientation information of the subject 16. More specifically, the OORM 100 automatically changes information that reflects the manual input received at step 202 to reflect the results of the automatic orientation determined at step 208. It should be realized that the orientation information entered by the operator, the orientation information generated by the OORM 100, and the various pictures generated by the cameras, may each be displayed on a display device.

Figure 7:
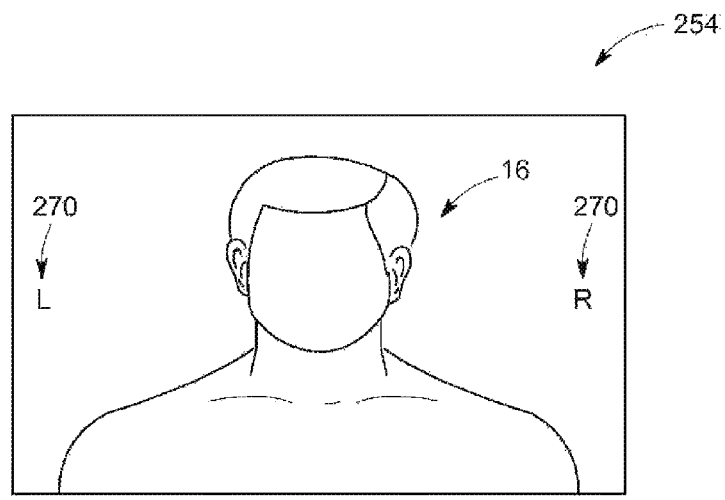
FIG. 7 is still another exemplary image that may be generated in accordance with various embodiments.

At 214, the subject 16 is scanned to generate an image 254 shown in FIG. 7. The image 254 of the subject 16 includes orientation indicia 270. In the exemplary embodiment, the orientation indicia 270 are based on the comparison performed as step 208. More specifically, the orientation indicia provide a visual indication of the orientation of the subject 16 on the image 254. The orientation indicia 270 may be embodied as a set of letters, such as "L" and "R" which represent the left side of the image and the right side of the image, respectively. It should be realized that the left and right sides of the image 270 is determined using the orientation information automatically determined at step 208. For example, assuming that the orientation of the subject 16 is supine/superior, then the letter L is placed on the left side of the image 254 and the letter R is placed on the right side of the image 254 as shown in FIG. 7. Optionally, if at step 208, it is automatically determined that the subject 16 is in the prone/superior position, then the letter L is placed on the right side of the image 254 and the letter R is placed on the left side of the image 254. The physician may then utilize the indicia 270 as a reference for the orientation of the subject during the scanning procedure and to perform a medical diagnosis based on this orientation.

Described herein is a system 10 that is configured to automatically determine an orientation of a subject being imaged. The system includes one or more cameras positioned on the CT gantry, or positioned in other locations in such a way that the subject's face is within the image field-of-view of the camera. In operation, the camera collects data on a subject's feature, such as the face, and using facial feature identification algorithms, identifies the face as right-side-up, or inverted, for example. The information collected by the camera and analyzed by a feature recognition module, may be used to either augment the operator's orientation information, or as substitute for the operator's orientation information.

A technical effect of at least one embodiment described herein is to automatically determine an orientation of a subject being imaged and based on the automatic determination to generate an image that includes orientation indicia that reflects the automatic determination. Various embodiments also improve the ability of a physician to perform a medical diagnosis in a reduced amount of time with increased accuracy.

FIG. 8 is a block schematic diagram of a portion of the multi-modality imaging system 10 shown in FIG. 1. In the exemplary embodiment, as discussed above, the multi-modality imaging system 10 includes the first modality 12, i.e. the CT imaging system. The CT imaging system 12 includes the gantry 20, the x-ray source 22, the detector array 24, the computer 30, the table 32, and the OORS 50. The OORS 50 includes at least one camera 60 which is coupled to the OORM 100.

The detector 24 includes a plurality of detector elements 310. Each detector element 310 produces an electrical signal, or output, that represents the intensity of an impinging X-ray beam and hence allows estimation of the attenuation of the beam as it passes through the subject 16. During a scan to acquire the x-ray projection data, the gantry 20 and the components mounted thereon rotate about a center of rotation 312. FIG. 8 shows only a single row of detector elements 310 (i.e., a detector row). However, the multislice detector array 24 includes a plurality of parallel detector rows of detector elements 310 such that projection data corresponding to a plurality of slices can be acquired simultaneously during a scan.

Rotation of the gantry 20 and the operation of the x-ray source 22 are governed by a control mechanism 314. The control mechanism 314 includes an x-ray controller 320 that provides power and timing signals to the x-ray source 22 and a gantry motor controller 322 that controls the rotational speed and position of the gantry 20. A data acquisition system (DAS) 324 in the control mechanism 314 samples analog data from detector elements 310 and converts the data to digital signals for subsequent processing. For example, the subsequent processing may include utilizing the OORS 50 to automatically determine an orientation of the subject 16 and to allow indicia to be provided on the image. An image reconstructor 326 receives the sampled and digitized x-ray data from the DAS 324 and performs high-speed image reconstruction. The reconstructed images are input to the computer 30 that stores the image in a storage device 328. Optionally, the computer 30 may receive the sampled and digitized x-ray data from the DAS 324 and perform various methods described herein using the OORS 50. The computer 30 also receives commands and scanning parameters from an operator via a console 330 that has a keyboard. The various commands may include, for example, the manual input from an operator that denotes the orientation of the subject 16 positioned on the table 32. An associated visual display unit 332 allows the operator to observe the reconstructed image and other data from computer.

The operator supplied commands and parameters are used by the computer 30 to provide control signals and information to the DAS 324, the x-ray controller 320 and the gantry motor controller 322. In addition, the computer 30 operates a table motor controller 334 that controls the motorized table 32 to position the subject 16 in the gantry 20. Particularly, the table 32 moves at least a portion of the subject 16 through the gantry opening 34 as shown in FIG. 1.

Referring again to FIG. 8, in one embodiment, the computer 30 includes a device 340, for example, a floppy disk drive, CD-ROM drive, DVD drive, magnetic optical disk (MOD) device, or any other digital device including a network connecting device such as an Ethernet device for reading instructions and/or data from a computer-readable medium 342, such as a floppy disk, a CD-ROM, a DVD or an other digital source such as a network or the Internet, as well as yet to be developed digital means. In another embodiment, the computer 30 executes instructions stored in firmware (not shown). The computer 30 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 22 and the detector array 24 are rotated with the gantry 20 within the imaging plane and around the subject 16 to be imaged such that the angle at which an x-ray beam 344 intersects the subject 16 constantly changes. A group of x-ray attenuation measurements, i.e., projection data, from the detector array 24 at one gantry angle is referred to as a "view". A "scan" of the subject 16 comprises a set of views made at different gantry angles, or view angles, during one revolution of the x-ray source 22 and the detector 24. In a CT scan, the projection data is processed to reconstruct an image that corresponds to a two dimensional slice taken through the subject 16.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software or which may be a non-transitory computer readable medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for determining an imaging orientation for a subject, the method comprising:
   receiving, at an imaging system, an input manually entered by an operator that indicates an orientation of a subject being imaged;
   automatically determining the orientation of the subject using a feature recognition system including a digital camera;
   comparing the received input to the automatically determined orientation; and
   generating an image, the image including orientation indicia based on the comparison.

2. The method of claim 1, further comprising:
   performing a scout scan of the subject; and
   automatically determining the orientation of the subject subsequent to the scout scan.

3. The method of claim 1, further comprising prompting an operator to input a second different orientation based on the comparison or to confirm the automatically determined orientation.

4. The method of claim 1, wherein the orientation indicia represents the automatically determined orientation.

5. The method of claim 1, wherein the orientation indicia includes an L symbol and an R symbol formed on the image.

6. The method of claim 1, wherein automatically determining the orientation further comprises determining if the subject is in a supine position, a prone position, a superior position or an inferior position.

7. The method of claim 1, wherein the feature recognition system comprises a facial recognition device, the method further comprising using the facial recognition device to automatically determine the orientation of the subject.

8. The method of claim 1, wherein the feature recognition system comprises a facial recognition device that is coupled to an external surface of the imaging system, the method further comprising using the facial recognition device to automatically determine the orientation of the subject prior to the subject being moved into the imaging system.

9. An object orientation recognition system (OORS) comprising:
   at least one feature recognition device; and
   an object orientation recognition module (OORM) configured to:
      receive a user input that indicates an orientation of a subject being imaged;
      receive an input from the feature recognition device that indicates the orientation of the subject;
      compare the user input to the input received from the feature recognition device; and
      generate an image, the image including orientation indicia based on the comparison.

10. The OORS of claim 9, wherein the at least one feature recognition device comprises a digital camera coupled to an exterior surface of a gantry.

11. The OORS of claim 9, wherein the OORM is further programmed to prompt an operator to input a second different orientation based on the comparison.

12. The OORS of claim 9, wherein the orientation indicia represents the automatically determined orientation.

13. The OORS of claim 9, wherein the OORM is further programmed to determine if the subject is in a supine position, a prone position, a superior position or an inferior position.

14. The OORS of claim 9, wherein the feature recognition system comprises a facial recognition device, the OORM being further programmed to use the facial recognition device to automatically determine the orientation of the subject.

15. The OORS of claim 9, wherein the feature recognition system comprises a facial recognition device that is coupled to an external surface of the imaging system, the OORM being further programmed to use the facial recognition device to automatically determine the orientation of the subject prior to the subject being moved into the imaging system.

16. An imaging system for generating an image of a subject, said imaging system comprising:
   an object orientation recognition system (OORS) comprising:
      a digital camera coupled to a gantry of the imaging system; and
      an object orientation recognition module (OORM) configured to:
         receive a user input that indicates an orientation of a subject being imaged;
         receive an input from the digital camera that indicates the orientation of the subject;
         compare the user input to the input received from the digital camera; and
         generate an image, the imaging including orientation indicia based on the comparison.

17. The imaging system of claim 16, wherein the OORM is further programmed to automatically determine the orientation of the subject subsequent to a scout scan.

18. The imaging system of claim 16, wherein the OORM is further programmed to prompt an operator to input a second different orientation based on the comparison.

19. The imaging system of claim 16, wherein the orientation indicia represents the automatically determined orientation.

20. The imaging system of claim 16, wherein the OORM is further programmed to determine if the subject is in a supine position, a prone position, a superior position or an inferior position.

* * * * *